United States Patent
Knippel et al.

(10) Patent No.: US 9,615,924 B2
(45) Date of Patent: Apr. 11, 2017

(54) STAGED DEPLOYMENT DEVICES AND METHODS FOR TRANSCATHETER HEART VALVE DELIVERY

(71) Applicant: St. Jude Medical, Cardiology Division, Inc., St. Paul, MN (US)

(72) Inventors: Bradley Charles Knippel, Lino Lakes, MN (US); Huisun Wang, Maple Grove, MN (US); Ralph Joseph Thomas, Champlin, MN (US); Jacob John Daly, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 140 days.

(21) Appl. No.: 14/329,406

(22) Filed: Jul. 11, 2014

(65) Prior Publication Data

US 2014/0324162 A1 Oct. 30, 2014

Related U.S. Application Data

(62) Division of application No. 13/234,782, filed on Sep. 16, 2011, now Pat. No. 8,778,019.

(Continued)

(51) Int. Cl.
*A61F 2/966* (2013.01)
*A61F 2/24* (2006.01)
(Continued)

(52) U.S. Cl.
CPC .............. *A61F 2/2436* (2013.01); *A61F 2/95* (2013.01); *A61F 2/962* (2013.01); *A61F 2/966* (2013.01);
(Continued)

(58) Field of Classification Search
CPC .......... A61F 2/2436; A61F 2/95; A61F 2/962; A61F 2/966
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| AU | 2011202175 B1 | 7/2011 |
| DE | 19857887 A1 | 7/2000 |

(Continued)

OTHER PUBLICATIONS

Japanese Office Action for Application No. 2013-525891 dated May 8, 2015.

(Continued)

*Primary Examiner* — Sarah W Aleman
(74) *Attorney, Agent, or Firm* — Lerner, David, Littenberg, Krumholz & Mentlik, LLP

(57) ABSTRACT

A delivery device for a collapsible heart valve includes an operating handle and a catheter assembly. The operating handle includes a frame defining a movement space therein, a carriage assembly moveable in a longitudinal direction within the movement space, and a coupler having locked and unlocked conditions, the coupler being operatively connected to the carriage assembly for movement therewith. The catheter assembly includes a shaft around which a valve-receiving compartment is defined, the shaft being operatively connected to one of the frame or the carriage assembly, and a distal sheath operatively connected to the carriage assembly for movement therewith between a closed condition adapted to maintain the valve in the compartment and an open condition adapted to fully deploy the valve.

16 Claims, 4 Drawing Sheets

Related U.S. Application Data

(60) Provisional application No. 61/384,032, filed on Sep. 17, 2010.

(51) Int. Cl.
*A61F 2/95* (2013.01)
*A61F 2/962* (2013.01)

(52) U.S. Cl.
CPC .............. *A61F 2002/9517* (2013.01); *A61F 2002/9534* (2013.01)

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,922,905 A | 5/1990 | Strecker |
| 5,391,172 A | 2/1995 | Williams et al. |
| 5,411,552 A | 5/1995 | Andersen et al. |
| 5,456,667 A | 10/1995 | Ham et al. |
| 5,480,423 A | 1/1996 | Ravenscroft et al. |
| 5,843,167 A | 12/1998 | Dwyer et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,488,702 B1 | 12/2002 | Besselink |
| 6,514,261 B1 | 2/2003 | Randall et al. |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,326,236 B2 | 2/2008 | Andreas et al. |
| 7,329,278 B2 | 2/2008 | Seguin et al. |
| 7,374,573 B2 | 5/2008 | Gabbay |
| 7,381,218 B2 | 6/2008 | Schreck |
| 7,399,315 B2 | 7/2008 | Iobbi |
| 7,419,501 B2 | 9/2008 | Chiu et al. |
| 7,452,371 B2 | 11/2008 | Pavcnik et al. |
| 7,476,244 B2 * | 1/2009 | Buzzard .................. A61F 2/95 606/108 |
| 7,510,572 B2 | 3/2009 | Gabbay |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| 7,993,384 B2 | 8/2011 | Wu et al. |
| 8,043,353 B2 | 10/2011 | Kaufmann et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,353,955 B2 | 1/2013 | Styrc et al. |
| 8,562,663 B2 | 10/2013 | Mearns et al. |
| 8,568,475 B2 | 10/2013 | Nguyen et al. |
| 8,778,019 B2 | 7/2014 | Knippel et al. |
| 8,790,386 B2 | 7/2014 | Dwork |
| 2002/0036220 A1 | 3/2002 | Gabbay |
| 2002/0183827 A1 | 12/2002 | Derus et al. |
| 2003/0050694 A1 | 3/2003 | Yang et al. |
| 2003/0130726 A1 | 7/2003 | Thorpe et al. |
| 2003/0144725 A1 | 7/2003 | Lombardi |
| 2004/0039436 A1 | 2/2004 | Spenser et al. |
| 2004/0049262 A1 | 3/2004 | Obermiller et al. |
| 2004/0093075 A1 | 5/2004 | Kuehne |
| 2004/0148009 A1 | 7/2004 | Buzzard et al. |
| 2004/0186563 A1 | 9/2004 | Lobbi |
| 2004/0210304 A1 | 10/2004 | Seguin et al. |
| 2004/0260390 A1 | 12/2004 | Sarac et al. |
| 2005/0004583 A1 | 1/2005 | Oz et al. |
| 2005/0049667 A1 | 3/2005 | Arbefeuille et al. |
| 2005/0080476 A1 | 4/2005 | Gunderson et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0240254 A1 | 10/2005 | Austin |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0167468 A1 | 7/2006 | Gabbay |
| 2006/0173532 A1 | 8/2006 | Flagle et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0156225 A1 | 7/2007 | George et al. |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0260301 A1 * | 11/2007 | Chuter .................. A61F 2/95 623/1.11 |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |

(56) References Cited

U.S. PATENT DOCUMENTS

| | | |
|---|---|---|
| 2008/0039934 A1 | 2/2008 | Styrc |
| 2008/0071369 A1 | 3/2008 | Tuval et al. |
| 2008/0082159 A1 | 4/2008 | Tseng et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0024137 A1 | 1/2009 | Chuter et al. |
| 2009/0054975 A1 | 2/2009 | del Nido et al. |
| 2009/0105798 A1 | 4/2009 | Koch |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1* | 5/2010 | Paul .................. A61F 2/2418 623/2.11 |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0224678 A1 | 9/2011 | Gabbay |
| 2011/0282425 A1 | 11/2011 | Dwork |
| 2011/0288626 A1 | 11/2011 | Straubinger et al. |
| 2011/0295216 A1 | 12/2011 | Miller |
| 2012/0022635 A1 | 1/2012 | Yamashita |
| 2012/0053574 A1 | 3/2012 | Murray, III et al. |
| 2012/0078352 A1 | 3/2012 | Wang et al. |
| 2012/0197391 A1 | 8/2012 | Alkhatib et al. |
| 2012/0310332 A1 | 12/2012 | Murray et al. |
| 2013/0030520 A1 | 1/2013 | Lee et al. |
| 2013/0138118 A1 | 5/2013 | Doyle |
| 2013/0231735 A1 | 9/2013 | Deem et al. |
| 2013/0304179 A1 | 11/2013 | Bialas et al. |
| 2014/0067050 A1 | 3/2014 | Costello et al. |
| 2014/0135909 A1 | 5/2014 | Carr et al. |

FOREIGN PATENT DOCUMENTS

| | | |
|---|---|---|
| DE | 20000659 U1 | 5/2001 |
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 A1 | 6/2004 |
| JP | 2001504717 A | 4/2001 |
| JP | 2004130074 | 4/2004 |
| JP | 2010504820 A | 2/2010 |
| JP | 2010526609 A | 8/2010 |
| JP | 2010531193 | 9/2010 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0018330 A1 | 4/2000 |
| WO | 0069368 A2 | 11/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008042266 A2 | 4/2008 |
| WO | 2008070797 A2 | 6/2008 |
| WO | 2008138584 A1 | 11/2008 |
| WO | WO 2008/138584 * 11/2008 ............... A61F 2/95 |
| WO | 2009001309 | 12/2008 |
| WO | 2009011866 A1 | 1/2009 |
| WO | 2009029199 A1 | 3/2009 |
| WO | 2009042196 A2 | 4/2009 |
| WO | 2009091509 A1 | 7/2009 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |
| WO | 2012026965 A2 | 3/2012 |
| WO | 2012036741 A2 | 3/2012 |

OTHER PUBLICATIONS

International Search Report and Written Opinion for Application No. PCT/US2014/064253 dated Feb. 3, 2015.
Australian Examination Report for Application No. 2011293898 dated Jul. 26, 2013.
Commonly owned co-pending U.S. Appl. No. 13/212,442, filed Aug. 18, 2011.
Commonly owned co-pending U.S. Appl. No. 13/216,124, filed Aug. 23, 2011.
Commonly owned co-pending U.S. Appl. No. 13/234,782, filed Sep. 16, 2011.
Commonly owned co-pending U.S. Appl. No. 13/788,820, filed Mar. 7, 2013.
International Search Report and Written Opinion for Application No. PCT/US2011/001450 dated Mar. 5, 2012.
International Search Report and Written Opinion for Application No. PCT/US2011/001615 dated Jul. 11, 2012.
International Search Report and Written Opinion for Application No. PCT/US2013/039407 dated Feb. 10, 2014.
International Search Report Application No. PCT/US2011/048963, dated Dec. 15, 2011.
International Search Report Application No. PCT/US2011/048967, dated Dec. 15, 2011.
International Search Report Application No. PCT/US2011/048989, dated Dec. 15, 2011.
International Search Report for Application No. PCT/US2011/001450 dated Mar. 5, 2012.
International Search Report for Application No. PCT/US2011/001597 dated Mar. 7, 2012.

(56) References Cited

OTHER PUBLICATIONS

Overview of PRE-CE Mark Transcatheter Aortic Valve Technologies (powerpoint—dated Jun. 1, 2010).

* cited by examiner

STAGED DEPLOYMENT DEVICES AND METHODS FOR TRANSCATHETER HEART VALVE DELIVERY

CROSS-REFERENCE TO RELATED APPLICATION

The present application is a divisional of U.S. patent application Ser. No. 13/234,782, filed Sep. 16, 2011, which claims the benefit of U.S. Provisional Patent Application Ser. No. 61/384,032, filed Sep. 17, 2010, entitled "Staged Deployment Devices and Methods for Transcatheter Heart Valve Delivery," the disclosures of which are hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheathe and reposition the valve.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

A delivery device for a collapsible prosthetic heart valve and a method of delivering a collapsible prosthetic heart valve in a patient are disclosed.

A delivery device for a collapsible prosthetic heart valve includes an operating handle, including a frame defining a movement space therein, a carriage assembly moveable in a longitudinal direction within the movement space, and a coupler having a locked condition in which the coupler is connected to the frame in a fixed position, and an unlocked condition in which the coupler is movable in the longitudinal direction within the movement space, the coupler being operatively connected to the carriage assembly for movement therewith. The delivery device also includes a catheter assembly, including a first shaft around which a compartment is defined, the first shaft being operatively connected to one of the frame or the carriage assembly, the compartment being adapted to receive the valve in an assembled condition, and a distal sheath operatively connected to the carriage assembly, the distal sheath being moveable between a closed condition adapted to maintain the valve in the assembled condition and an open condition adapted to fully deploy the valve, wherein movement of the carriage assembly in the longitudinal direction in the movement space moves the distal sheath between the closed condition and the open condition.

The coupler may be selectively lockable to the frame in any of a plurality of fixed positions in the longitudinal direction. The coupler may include a releasable pin and the frame may have a plurality of fixed notches, the pin being engageable in one of the notches to lock the coupler to the frame. The coupler may be selectively lockable to the frame in positions that correspond to positions of the distal sheath between the closed condition and the open condition. The operating handle may further include a threaded rod extending from the carriage assembly through the coupler, and a deployment actuator threadedly engaged with the threaded rod and longitudinally constrained relative to the coupler, such that rotation of the deployment actuator may move the carriage assembly in the longitudinal direction in the movement space. Rotation of the deployment actuator in a first direction may move the carriage assembly proximally in the longitudinal direction in the movement space, and rotation of the deployment actuator in a second direction opposite the first direction may move the carriage assembly distally in the longitudinal direction in the movement space.

The delivery device may further include a latch mechanism adapted to releasably fix the coupler relative to the frame at any of a plurality of longitudinal positions in the movement space. The operating handle may further include a resheathing lock having a locked position and an unlocked position, the resheathing lock in the locked position limiting movement of the carriage assembly in the longitudinal direction to a stop position in the movement space, and the resheathing lock in the unlocked position permitting movement of the carriage assembly beyond the stop position, wherein movement of the carriage assembly to the stop position may move the distal sheath to a condition between the closed condition and the open condition so that the valve is not fully deployed. The frame may include a slot and the resheathing lock may include a retractable pin that is engaged in the slot when the resheathing lock is in the locked position, and a stop member located within the slot may define the stop position. The stop member may be longitudinally moveable within the slot, such that movement of the stop member may change the location of the stop position relative to the frame.

The compartment may have a first length and the stop position in the movement space may correspond to a travel distance of the carriage assembly, the travel distance being less than the first length. The collapsible prosthetic heart valve may have a second length and the travel distance may be between about 80% and about 90% of the second length. The first shaft may be operatively connected to the frame, the catheter assembly further including an outer shaft connecting the carriage assembly to the distal sheath and at least partially surrounding the first shaft. The first shaft may be operatively connected to the frame, and the operating handle may further include a mechanism adapted to move the first shaft proximally relative to the frame. The mechanism may include a threaded rod operatively connected to the first shaft and extending in the longitudinal direction, and a nut threadedly engaged with the threaded rod and longitudinally constrained relative to the frame.

The first shaft may be operatively connected to the carriage assembly, the catheter assembly further including an outer shaft connecting the frame to the compartment and at least partially surrounding the first shaft. The first shaft may be operatively connected to the carriage assembly, and the operating handle may further include a mechanism adapted to move the first shaft proximally relative to the carriage assembly. The mechanism may include a threaded rod operatively connected to the first shaft and extending in the longitudinal direction, and a nut threadedly engaged with the threaded rod and longitudinally constrained relative to the carriage assembly.

A method of delivering a collapsible prosthetic heart valve in a patient includes providing a delivery device having a catheter assembly and an operating handle, the catheter assembly including a compartment adapted to receive the valve in an assembled condition, the operating handle including a frame defining a movement space therein, a carriage assembly moveable in a longitudinal direction within the movement space, and a coupler operatively connected to the carriage assembly for movement therewith. The method also includes loading the valve into the compartment of the catheter assembly, the compartment and the valve being covered by a distal sheath of the catheter assembly, inserting the catheter assembly into the patient, positioning the valve at a target location within the patient, partially deploying the valve by moving the carriage assembly of the operating handle in a first longitudinal direction along a first portion of the movement space, and fully deploying the valve by translating the coupler of the operating handle to continue movement of the carriage assembly in the first longitudinal direction along a second portion of the movement space.

The operating handle may further include a threaded rod extending from the carriage assembly through the coupler, and a deployment actuator threadedly engaged with the threaded rod and longitudinally constrained relative to the coupler, and the partially deploying step may include rotating the deployment actuator. The operating handle may further include a resheathing lock having a locked position and an unlocked position, the resheathing lock in the locked position limiting movement of the carriage assembly in the longitudinal direction to a stop location in the movement space, the resheathing lock in the unlocked position permitting movement of the carriage assembly beyond the stop location. The method may further include adjusting a position of the resheathing lock in the longitudinal direction to set the stop location in the movement space. The method may further include resheathing the valve by moving the carriage assembly in a second longitudinal direction opposite the first longitudinal direction.

The catheter assembly may further include a first shaft around which the compartment is defined and an outer shaft connecting the carriage assembly to the distal sheath and at least partially surrounding the first shaft, the first shaft may be operatively connected to the frame, the distal sheath may be operatively connected to the carriage assembly, and the steps of partially deploying the valve and fully deploying the valve may each include moving the outer shaft proximally relative to the frame. The catheter assembly may further include a first shaft around which the compartment is defined, the first shaft may be operatively connected to the frame, the distal sheath may be operatively connected to the carriage assembly, and the resheathing step may include moving the first shaft proximally relative to the frame and the distal sheath.

The operating handle may further include a threaded rod operatively connected to the first shaft and extending in the longitudinal direction, and a nut threadedly engaged with the threaded rod and longitudinally constrained relative to the frame, and the step of moving the first shaft may include rotating the nut about the threaded rod. The operating handle may further include a resheathing lock having a locked position and an unlocked position, the resheathing lock in the locked position limiting movement of the carriage assembly in the longitudinal direction to a stop location in the movement space, the resheathing lock in the unlocked position permitting movement of the carriage assembly beyond the stop location, and the step of moving the first shaft may be performed with the resheathing lock in the locked position.

The catheter assembly may further include a first shaft around which the compartment is defined and an outer shaft connecting the frame to the compartment and at least partially surrounding the first shaft, the first shaft and the distal sheath may be operatively connected to the carriage assembly, and the steps of partially deploying the valve and fully deploying the valve may each include moving the first shaft distally relative to the frame. The catheter assembly may further include a first shaft around which the compartment is defined, the first shaft and the distal sheath may be operatively connected to the carriage assembly, and the resheathing step may include moving the first shaft proximally relative to the carriage assembly.

The operating handle may further include a threaded rod operatively connected to the first shaft and extending in the longitudinal direction, and a nut threadedly engaged with the threaded rod and longitudinally constrained relative to the carriage assembly, and the step of moving the first shaft may include rotating the nut about the threaded rod. The operating handle may further include a resheathing lock having a locked position and an unlocked position, the resheathing lock in the locked position limiting movement of the carriage assembly in the longitudinal direction to a stop location in the movement space, the resheathing lock in the unlocked position permitting movement of the carriage assembly beyond the stop location, and the step of moving the first shaft may be performed with the resheathing lock in the locked position. The target location within the patient may be the native aortic annulus of the patient. The distal sheath of the delivery device may be inserted through a femoral artery of the patient. The distal sheath of the delivery device may be inserted through the apex of the heart of the patient.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user.

Figure 1:
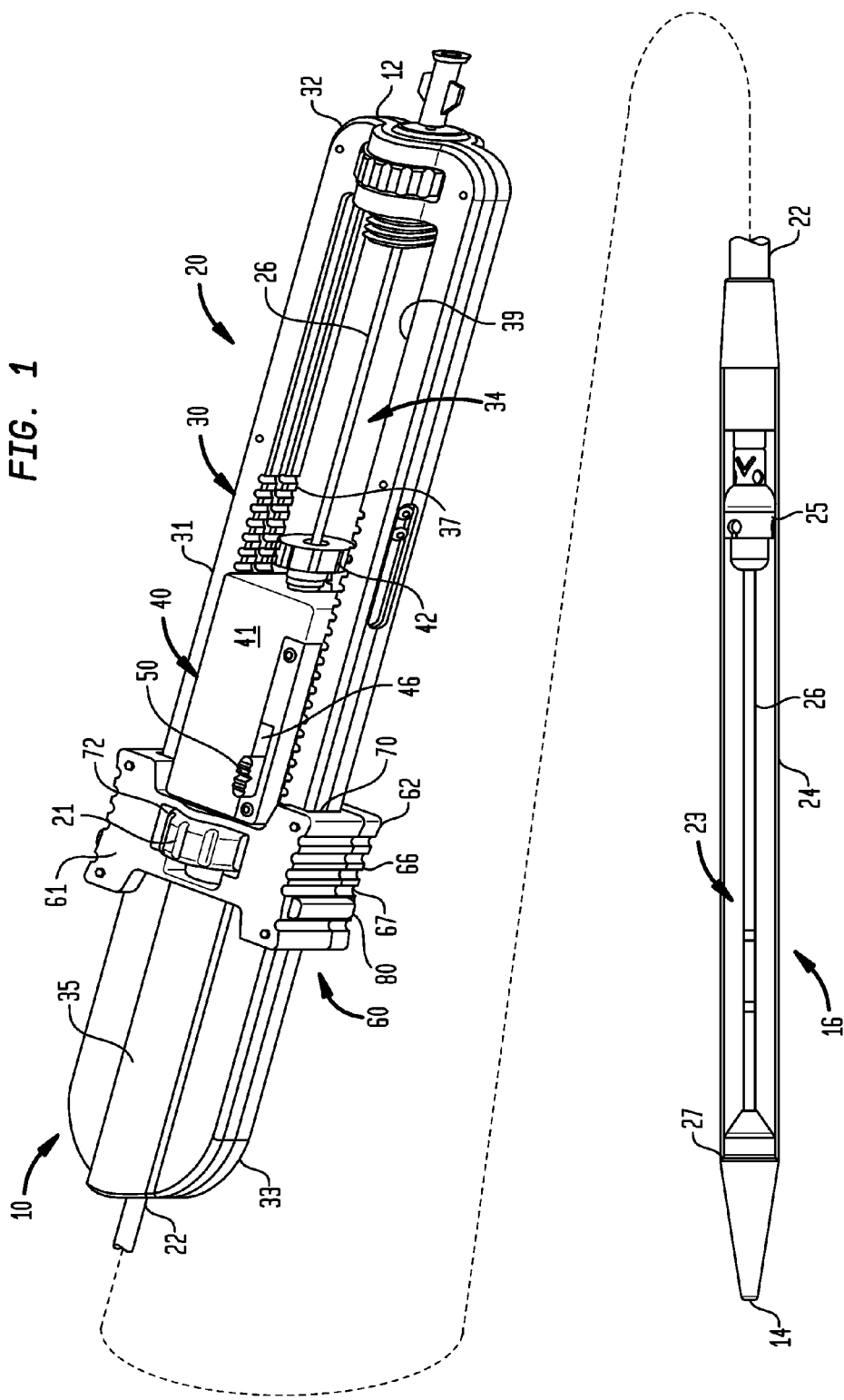
FIG. 1 is a perspective view of an operating handle for a transfemoral delivery device for a collapsible prosthetic heart valve, shown with a side elevation of the distal portion of a transfemoral catheter assembly.
Figure 2:
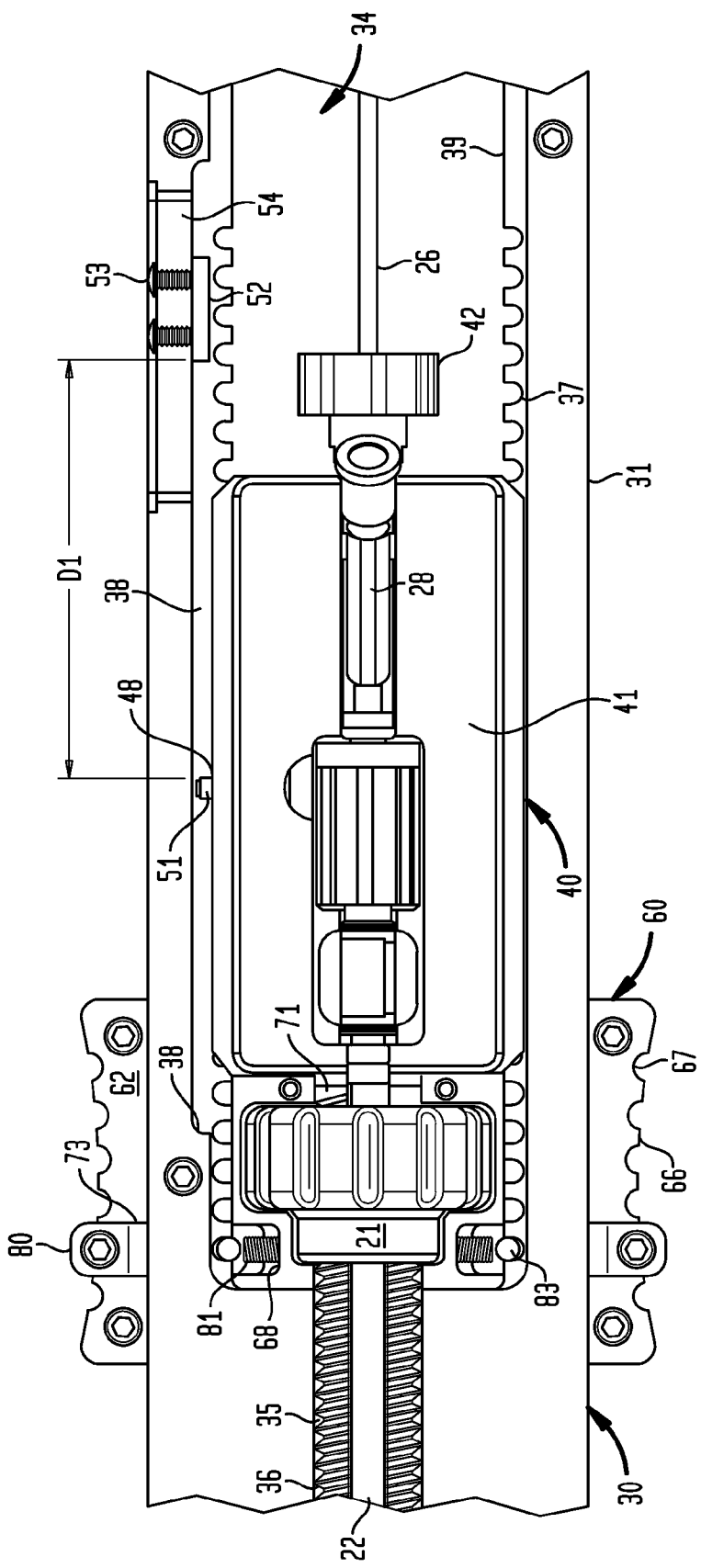
FIG. 2 is an enlarged bottom plan view of a portion of the handle of FIG. 1.

Referring now to FIGS. 1 and 2 to illustrate the structure and function of the present invention, an exemplary transfemoral delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. The delivery device 10 extends from a proximal end 12 to a distal tip 14. The catheter assembly 16 is adapted to receive a collapsible prosthetic heart valve (not shown) in a compartment 23 defined around an inner shaft 26 and covered by a distal sheath 24.

The inner shaft 26 extends through the operating handle 20 to the distal tip 14 of the delivery device, and includes a retainer 25 affixed thereto at a spaced distance from distal tip 14 and adapted to hold a collapsible prosthetic valve in the compartment 23.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20 in a manner to be described. The distal end 27 of the distal sheath 24 abuts the distal tip 14 when the distal sheath is fully covering the compartment 23, and is spaced apart from the distal tip 14 when the compartment 23 is at least partially uncovered.

The operating handle 20 is adapted to control deployment of a prosthetic valve located in the compartment 23 by permitting a user to selectively slide the outer shaft 22 proximally or distally relative to the inner shaft 26, thereby respectively uncovering or covering the compartment with the distal sheath 24. The proximal end of the inner shaft 26 is operatively coupled to an outer frame 30 of the operating handle 20 (the longitudinal position of the inner shaft relative to the frame can be adjusted, as described below), and the proximal end of the outer shaft 22 is affixed to a carriage assembly 40 of the operating handle that is slidable along a longitudinal axis of the frame, such that a user can selectively slide the outer shaft relative to the inner shaft by sliding the carriage assembly relative to the frame.

A hemostasis valve 28 includes an internal gasket adapted to create a seal between the inner shaft 26 and the proximal end of the outer shaft 22. A gasket adjustment wheel 42 in the carriage assembly 40 is adapted to adjust the strength of this seal. For example, the gasket inside the hemostasis valve 28 may be in the shape of an O-ring located around the inner shaft 26, or between the O-ring and the inner surface of the outer shaft 22. When the strength of the seal is insufficient, there may be a gap between the O-ring and the outer surface of the inner shaft 26, and/or between the O-ring and the inner surface of the outer shaft 22. To eliminate this gap, a user can turn the gasket adjustment wheel 42 to place a compressive force on the O-ring in the longitudinal direction of the inner shaft 26, thereby compressing the O-ring longitudinally and expanding the O-ring radially. The radially-expanded O-ring can fill any gap between the O-ring and the outer surface of the inner shaft 26 or the inner surface of the outer shaft 22, thereby creating a liquid-proof seal therebetween.

The frame 30 includes a pair of side rails 31 joined at the proximal end 12 by a proximal end member 32 and joined at the distal end by a distal end member 33. Collectively, the side rails 31, the end member 32, and the end member 33 define an elongated space 34 in the frame 30 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted from around the prosthetic valve. An enlarged bore 35 in the end member 33 is sized to freely and slidingly receive a threaded rod 36 extending from the distal end of the carriage assembly 40, as described below. The enlarged bore 35 has a smooth interior surface and an inner diameter slightly larger than the outer diameter of the threaded rod 36 (a longitudinal cross-section of the threaded rod positioned inside of the enlarged bore is shown in FIG. 2).

The carriage assembly 40 includes a main body 41 and the threaded rod 36 extending distally therefrom along the longitudinal axis of the frame 30. The threaded rod 36 preferably is longer than the anticipated maximum travel distance of the carriage assembly 40 within the elongated space 34 (e.g., at least about 50 mm), such that the threaded rod 36 does not fully withdraw from the enlarged bore 35 during deployment of the prosthetic valve.

A coupler 60 includes a top member 61 and a bottom member 62 joined to one another so as to define a pair of channels 70 extending longitudinally therebetween, the channels being sized and shaped to slidingly receive the side rails 31 of the frame 30 therethrough. The lateral sides 66 of the coupler 60 may include vertically-extending ridges 67 to facilitate grasping and moving of the coupler. The top member 61 and the bottom member 62 further define a central bore 71 extending longitudinally therebetween and sized to freely and slidingly receive the threaded rod 36 therethrough, as well as a pocket 72 extending vertically therethrough for receiving a deployment actuator 21 in threaded engagement with the threaded rod. The pocket 72 is sized and shaped to receive the deployment actuator 21 with minimal clearance, such that the deployment actuator remains substantially fixed relative to the coupler 60 as it is rotated on the threaded rod 36. That is, rotation of the deployment actuator 21 in one direction (either clockwise or counterclockwise depending on the orientation of the threads on the threaded rod 36) causes the threaded rod 36 to move proximally within the central bore 71, at the same time pushing the carriage assembly 40 proximally through the elongated space 34. Similarly, rotation of the deployment actuator 21 in the opposite direction causes the threaded rod 36 to move distally within the central bore 71, at the same time pulling the carriage assembly distally through the elongated space 34.

The coupler 60 may include a pair of locking members 80 positioned on opposite lateral sides 66 thereof. Each locking member 80 may be slidably received in a socket 73 extending laterally inward from the lateral sides 66 of the coupler 60 to an end surface 68. The locking members 80 are biased laterally outward from the lateral sides 66 by a spring 81 positioned between the inner end of the locking member and the end surface 68 of the socket 73. A pin 83 extending upward from each locking member 80 is sized to be selectively engaged in one of a plurality of notches 37 formed in an inner surface 39 of each side rail 31. The engagement of the pins 83 in the notches 37 locks the coupler 60 and the deployment actuator 21 to the frame 30, so as to permit rotation of the deployment actuator in both directions without translation of same within the space 34. Simultaneously depressing both locking members 80 against the bias of the springs 81 causes the pins 83 to move out of engagement with the notches 37, thereby freeing the coupler 60 and the deployment actuator 21 to move longitudinally relative to the frame 30.

The capability of the deployment actuator 21 to become longitudinally constrained relative to the frame 30 may provide a user with the ability to carefully control movement of the carriage assembly 40 both proximally within the space 34 during a valve deployment operation, and distally within the space 34 during a resheathing operation, as described more fully below. The capability of the deployment actuator 21 to freely move longitudinally relative to the frame 30 enables gross movement of the carriage assembly 40 proximally or distally within the space 34 without the mechanical advantage provided by the deployment actuator. Such movement is not easily controllable, but rather is subject to the "touch and feel" of the user.

The carriage assembly 40 may include a resheathing lock adapted to limit the longitudinal movement of the carriage assembly within the outer frame 30, thereby preventing a user from completing the deployment of a prosthetic valve when unintended. The resheathing lock includes a control member 50 that is longitudinally slidable in a slot 46 between a distal position (shown in FIG. 1) and a proximal position (not shown).

The control member 50 is operatively coupled to a pin 51 that projects laterally through an aperture 48 in the main body 41 of the carriage assembly 40. With the carriage assembly 40 in its initial position (shown in FIG. 1), the aperture 48 may be aligned with the distal end 38' of a longitudinally extending slot 38 in the side rail 31 of the frame 30, or the aperture may be aligned with another location within the slot (e.g., in FIG. 2, the aperture is aligned with a location near the center of the slot). When the control member 50 is in its distal most position (shown in FIG. 1), the pin 51 will extend through the aperture 48 and into the slot 38. Such condition will enable the carriage assembly 40 to move longitudinally within the frame 30 between an initial position at which the distal end of the carriage assembly contacts the coupler 60 and a position at which the pin 51 contacts a stop member 52 that is longitudinally adjustable within the slot, as discussed below. In the initial position, the pin 51 may contact the distal end 38' of the slot 38 or may be spaced therefrom by a predetermined distance. Movement of the control member 50 proximally causes the pin 51 to move laterally inward until the pin is no longer engaged in the slot 38. This action thus frees the carriage assembly 40 for further proximal movement relative to the frame 30, thereby permitting full deployment of a prosthetic valve from the compartment 23.

While essentially any mechanism usable for controlling lateral retraction of a pin can be used to operatively couple the control member 50 to the pin 51 described herein, example cam-based mechanisms that can be employed are discussed in greater detail in co-pending U.S. Patent Application No. 61/376,425, filed on Aug. 24, 2010, the disclosure of which is hereby incorporated by reference herein.

An initial distance D1 that the carriage assembly 40 can travel before being limited by the stop member 52 may be adjustable. That is, the stop member 52 may be fixed to the side rail 31 of the frame 30 by screws 53 extending through a longitudinally extending slot 54 in the side rail. By loosening the screws 53, the stop member 52 may be slid proximally or distally within slot 38 to a desired position, at which the screws may be retightened to lock the stop member in place.

The initial distance D1 that the carriage assembly 40 can travel before being limited by the stop member 52 may depend on the structure of the particular prosthetic valve to be deployed. Preferably, the initial travel distance D1 of the carriage assembly 40 is about 3 mm to about 5 mm less than the crimped valve length. Alternatively, the initial travel distance D1 of the carriage assembly 40 may be about 40 mm to about 45 mm, which is about 80% to about 90% of the length of an exemplary 50 mm valve. In other arrangements, the initial distance D1 that the carriage assembly 40 can travel can be determined as a percentage of the length of the prosthetic valve and/or the compartment 23, including, for example, 50%, 60%, 70%, 75%, 85%, or 95%.

Figure 3:
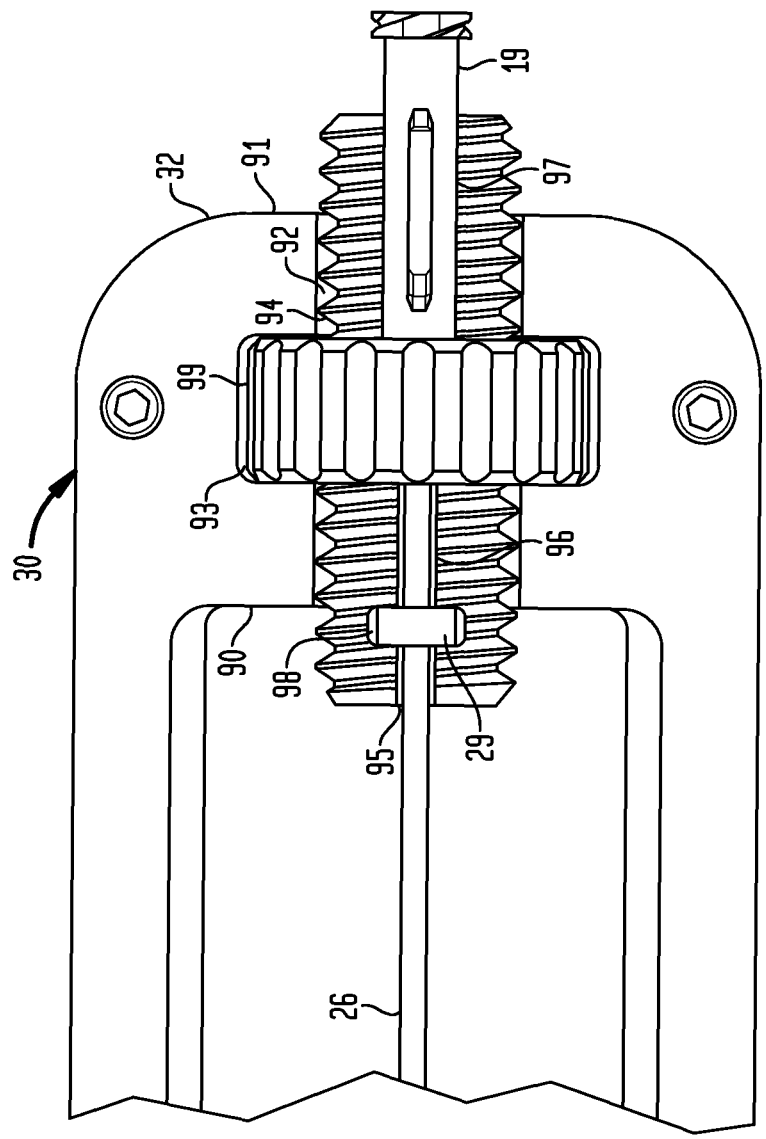
FIG. 3 is an enlarged bottom plan view of another portion of the handle of FIG. 1, with portions removed to illustrate the interior thereof.

Referring now to FIG. 3, the proximal end member 32 of the frame 30 has an inside frame wall 90 that defines the proximal end of the elongated space 34, and an outside frame wall 91 that defines the proximal end 12 of the delivery device 10. The proximal end member 32 includes a central bore 92 extending longitudinally therethrough between the inside frame wall 90 and the outside frame wall 91 and sized to freely and slidingly receive a threaded rod 94 therethrough. A pocket 93 extends vertically through the proximal end member 32 for receiving a shaft adjustment nut 99 in threaded engagement with the threaded rod 94. The pocket 93 is sized and shaped to receive the shaft adjustment nut 99 with minimal clearance, such that the shaft adjustment nut remains substantially fixed relative to the frame 30 as it rotates on the threaded rod 94. Accordingly, rotation of the shaft adjustment nut 99 in one direction (either clockwise or counterclockwise depending on the orientation of the threads on the threaded rod 94) causes the threaded rod 94 to move proximally within the central bore 92, and rotation of the shaft adjustment nut 99 in the opposite direction causes the threaded rod 94 to move distally within the central bore 92.

The threaded rod 94 has an interior bore 95 extending longitudinally therethrough. A distal portion 96 of the bore 95 has an inner diameter equal to or slightly larger than the outer diameter of the inner shaft 26. A proximal portion 97 of the bore 95 has an inner diameter equal to or slightly larger than a hub 19 fixed to the proximal end of the inner shaft 26. An annular rib 29 extending around the inner shaft 26 may be captured within an annular groove 98 formed in the distal portion 96 of the bore 95 to fix the inner shaft 26 longitudinally to the threaded rod 94. As a result, as the threaded rod 94 moves longitudinally upon rotation of the shaft adjustment nut 99, the inner shaft 26 will move longitudinally along with it.

The operation of the present invention to deploy a prosthetic valve will now be described. To load the delivery device 10 with a collapsible prosthetic valve, a user can retract the distal sheath 24 to expose the compartment 23, place the valve around the inner shaft 26, couple the proximal end of the valve to the retainer 25, compresses or crimp the valve, and slide the distal sheath 24 over the compartment, which holds the valve in a compressed state. In this starting condition, the handle 20 will be in an initial state with the carriage assembly 40 at its distal most position within the frame 30, the resheathing lock will be in its locked position to prevent full deployment, and the coupler 60 will be at its distal most position within the frame.

To use the operating handle 20 to deploy a prosthetic valve that has been compressed and inserted in the compartment 23 and covered by the distal sheath 24, a user may rotate the deployment actuator 21, causing the carriage assembly 40 to slide proximally within the elongated space 34 in the frame 30. Because the distal sheath 24 is affixed to the outer shaft 22, which in turn is affixed to the carriage assembly 40, and because the inner shaft 26 is fixed to the frame 30 (although the longitudinal position of the inner shaft relative to the frame can be adjusted, as described above), sliding the carriage assembly proximally relative to the frame will retract the distal sheath proximally from the compartment 23, thereby exposing and initiating deployment of the valve located therein.

It will be appreciated that the user may initiate the deployment process without use of the deployment actuator 21 by simply squeezing the locking members 80 inwardly towards one another to release the coupler 60, and simultaneously pulling the coupler proximally within the frame 30. As the coupler 60 is pulled proximally within the frame 30, the linking of the coupler to the carriage assembly 40 through the threaded rod 36 and the deployment actuator 21 results in a concomitant proximal movement of the carriage assembly. Such action requires significant pulling force in order to overcome the frictional forces acting on the outer shaft 22 and the distal sheath 24. For that reason, the use of the deployment actuator 21 to begin retracting the distal sheath 24 is preferred since such use provides the user with a mechanical advantage to overcome the aforementioned frictional forces, thereby providing the user with much greater control of the deployment process.

After the distal sheath 24 has been partially retracted from the compartment 23, the portion of the prosthetic valve that includes tissue may be fully exposed, so that the frictional forces acting between the valve and the distal sheath are greatly reduced. At this point, it is preferred that the user continue the deployment process without use of the deployment actuator 21 by squeezing the locking members 80 inwardly towards one another while pulling the coupler 60 and the carriage assembly 40 proximally within the frame 30. Although the user will not have a mechanical advantage without using the deployment actuator 21 to move the carriage assembly 40 proximally, continuing the deployment process while squeezing the locking members 80 may allow such process to be completed more quickly.

In any event, since the resheathing lock is in the locked position, movement of the carriage assembly 40 proximally may continue only until the pin 55 contacts the stop member 52. At this point, the distal sheath 24 will not be fully withdrawn from the compartment 23, and the prosthetic valve will not be fully deployed.

When the deployment procedure has reached this juncture, the user can evaluate the position of the valve and determine whether the annulus end of the valve is properly aligned relative to the patient's aortic annulus. If repositioning is desired, the user may resheathe the valve by rotating the deployment actuator 21 in the direction opposite that used for deployment. Such rotation will cause the threaded rod 36 to progress distally through the deployment actuator 21 until the carriage assembly 40 has reached the starting condition shown in FIGS. 1 and 2, thereby moving the distal sheath 24 distally over the compartment 23 and the partially deployed valve and recollapsing the expanded part of the valve. With the valve resheathed, the user can reposition the delivery device 10 and commence the deployment procedure once again.

If, during deployment, the coupler 60 has been moved proximally away from the distal end member 33 of the frame 30, it will be appreciated that the user may partially or fully resheathe the valve without use of the deployment actuator 21 by simply squeezing the locking members 80 inwardly towards one another to release the coupler 60, and simultaneously pushing the coupler distally within the frame 30. As the coupler 60 is pushed distally within frame 30, the linking of the coupler to the carriage assembly results in a concomitant distal movement of the carriage assembly. Such action requires significant pushing force in order to overcome the frictional forces acting on the outer shaft 22 and the distal sheath 24, as well as the resilient forces which expand the stent portion of the valve. For that reason, the use of the deployment actuator 21 to replace the distal sheath 24 over the compartment 23 is preferred since such use provides the user with a mechanical advantage to overcome the aforementioned forces.

If, during deployment, the user has partially deployed and then resheathed the valve, the outer shaft 22 and/or the inner shaft 26 may have become temporarily or permanently deformed, such that the respective distal ends thereof may be longitudinally displaced relative to one another. During resheathing, the aforementioned frictional forces will tend to longitudinally compress the outer shaft 22 and stretch the inner shaft 26, for example, by a total length distributed between the inner and outer shafts of about 3 mm to about 10 mm. Such permanent deformation of these components may result in an inability of the distal sheath 24 to completely cover the compartment 23 such that the distal end 27 of the distal sheath may not extend far enough to abut the distal tip 14.

To adjust the relative longitudinal positions of the distal tip 14 and the distal sheath 24, the user may rotate the shaft adjustment nut 99, causing the threaded rod 94 and the inner shaft 26 affixed thereto to slide proximally relative to the frame 30. Because the distal sheath 24 is connected to the outer shaft 22 which, in turn, is connected to the inner carriage 40 and thus fixed relative to the frame 30, and because the distal tip 14 is connected to the inner shaft 26, sliding the inner shaft proximally relative to the frame will slide the distal tip proximally relative to the distal sheath, which may continue until the distal tip contacts the distal end 27 of the distal sheath and the compartment 23 is completely covered.

Once the valve has been properly positioned relative to the aortic annulus, the user may complete the deployment process. To do so, the user slides the control member 50 of the resheathing lock from the locked position to the unlocked position, thereby retracting the pin 51 so that the carriage assembly 40 is free to continue its movement proximally beyond the stop member 52. The user can continue to slide the carriage assembly 40 proximally to complete the deployment of the valve by rotating the deployment actuator 21 or by squeezing the locking members 80 inwardly towards one another while grasping the coupler 60 and pulling same proximally within the frame 30. When the valve is unsheathed, the stent portion of the valve self-expands and is disengaged from the retainer 25, thereby releasing the valve from the catheter assembly 16.

Figure 4:
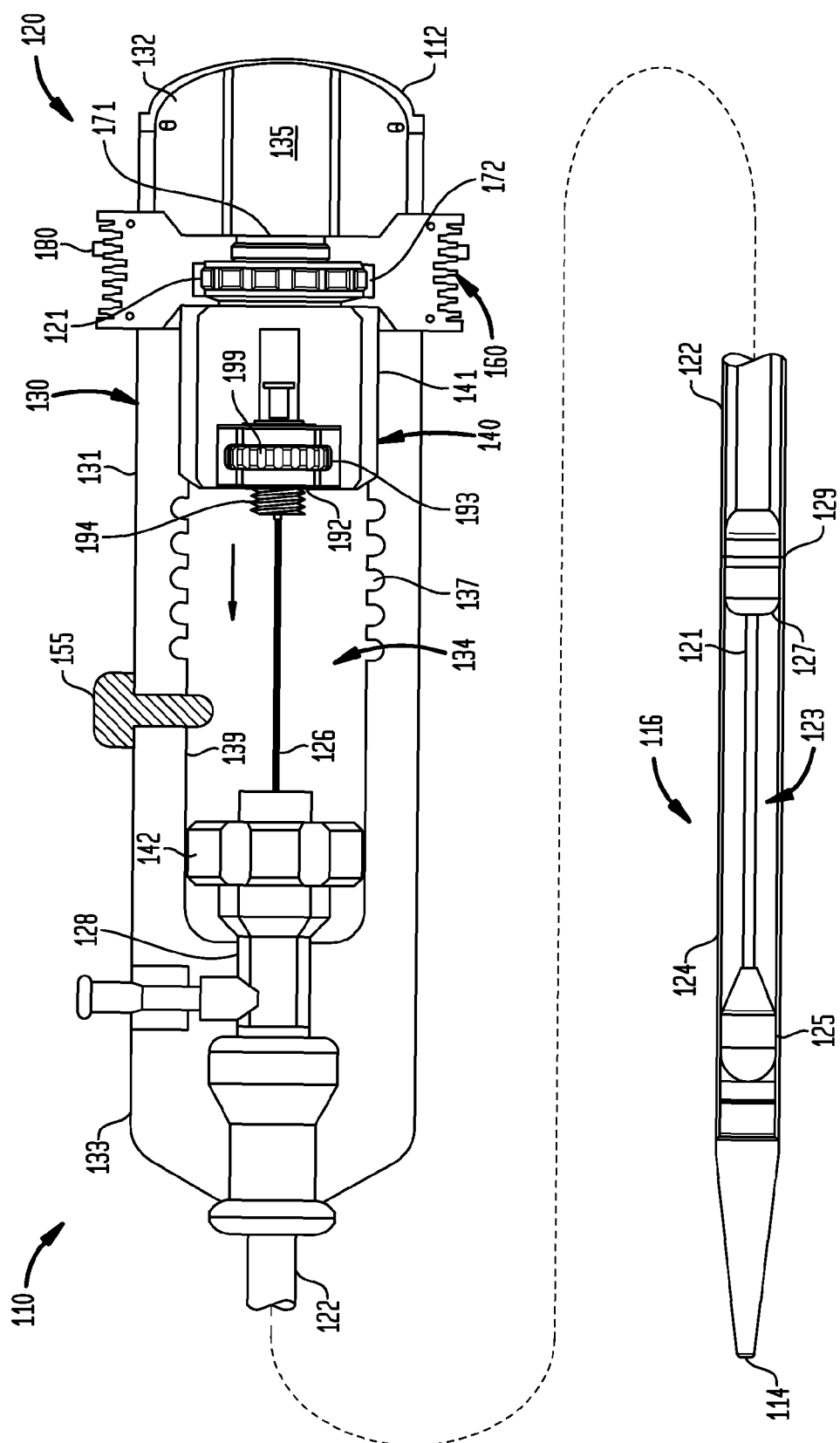
FIG. 4 is a bottom plan view of an operating handle for a transapical delivery device for a collapsible prosthetic heart valve, shown with a side elevation of the distal portion of a transapical catheter assembly.

Referring now to FIG. 4, an exemplary transapical delivery device 110 for a collapsible prosthetic heart valve (or other types of self-expanding collapsible stents) has a catheter assembly 116 for delivering the heart valve to and deploying the heart valve at a target location, and an operating handle 120 for controlling deployment of the valve from the catheter assembly. The delivery device 110 extends from a proximal end 112 to a distal tip 114. The catheter assembly 116 is adapted to receive a collapsible prosthetic heart valve (not shown) in a compartment 123 defined around a tubular support shaft 121 and covered by a distal sheath 124.

The support shaft 121 extends between a pair of spaced retainers 125 and 127 affixed thereto and defining the ends of the compartment 123. A collapsible prosthetic valve may be assembled around the support shaft 121 and between the retainers 125 and 127 in the compartment 123.

The distal sheath 124 surrounds the support shaft 121 and is slidable relative to the support shaft such that it can selectively cover or uncover the compartment 123. The distal sheath 124 is affixed at its distal end to the distal tip 114, and its proximal end 129 abuts the retainer 127 when the distal sheath is fully covering the compartment 123, as shown in FIG. 4. The proximal end 129 of the distal sheath 124 is spaced apart from the retainer 127 when the compartment 123 is at least partially uncovered.

The delivery device further includes an outer shaft 122, the proximal end of which is connected to the operating handle 120, and the distal end of which is connected to the retainer 127. An inner shaft 126 extends through the operating handle 120 and the support shaft 121 to the distal tip 114. The connection of the distal sheath 124 to the distal tip 114 thus enables the inner shaft 126 to control the movement of the distal sheath both proximally and distally.

The operating handle 120 is adapted to control deployment of a prosthetic valve located in the compartment 123 by permitting a user to selectively slide the inner shaft 126 and the attached distal sheath 124 distally or proximally relative to the support shaft 121, thereby respectively uncovering or covering the compartment with the distal sheath. The proximal end of the outer shaft 122 is connected to an outer frame 130 of the operating handle 120, and the proximal end of the inner shaft 126 is connected to a carriage assembly 140 of the operating handle that is slidable along a longitudinal axis of the frame (although the longitudinal position of the inner shaft relative to the carriage assembly can be adjusted, as described below), such that a user can selectively slide the inner shaft relative to the outer shaft by sliding the carriage assembly relative to the frame. A hemostasis valve 128 provides an internal gasket adapted to create a seal between the inner shaft 126 and the proximal end of the outer shaft 122. The strength of this seal may be adjusted by a gasket adjustment wheel 142 that functions in substantially the same manner as the adjustment wheel 42 described above.

The frame 130 includes a pair of side rails 131 joined at the proximal end 112 by an end member 132 and joined at the distal end by an end member 133. Collectively, the side rails 131, the end member 132, and the end member 133 define an elongated space 134 in the frame 130 in which the carriage assembly 140 may travel. An enlarged bore 135 in the proximal end member 132 is sized to freely and slidingly receive a threaded rod (not shown in FIG. 4) extending from the proximal end of the carriage assembly 140, as described below. The carriage assembly 140 includes a main body 141 and the threaded rod extending proximally therefrom along the longitudinal axis of the frame 130.

A coupler 160 may be configured in much the same manner as the coupler 60 described above with reference to FIGS. 1 and 2, and the locking members 180 included in the coupler 160 may have the same structure and function as the locking members 80 described above. That is, the locking members 180 may each include a pin (not shown) that cooperates with the notches 137 formed on an inner surface 139 of each side rail 131 to lock the coupler 160 in a fixed longitudinal position relative to the frame 130. However, the coupler 160 is slidably engaged with the side rails 131 proximally of the carriage assembly 140 and distally of the proximal end member 132. A deployment actuator 121 located within a pocket 172 in the coupler 160 is threadedly engaged with the threaded rod extending from the carriage assembly 140. Rotation of the deployment actuator 121 in one direction (either clockwise or counterclockwise depending on the orientation of the threads on the threaded rod of the carriage assembly 140) causes the threaded rod to move proximally within a central bore 171 of the coupler 160, at the same time pulling the carriage assembly 140 proximally toward the proximal end member 132. Similarly, rotation of the deployment actuator 121 in the opposite direction causes the threaded rod of the carriage assembly 140 to move distally within the central bore 171, at the same time pushing the carriage assembly distally through the elongated space 134.

The operating handle 120 may also include a resheathing lock mechanism for preventing the user from accidentally completing the deployment of a valve located in the compartment 123. The resheathing lock mechanism may include a resheathing lock member 155 that projects through the side rail 131 of the frame 130 and into the elongated space 134 so as to obstruct the path of travel of the carriage assembly 140 in the distal direction. As such, the resheathing lock member 155 defines the initial distance that the carriage assembly 140 may travel before full deployment of the valve occurs. The resheathing lock member 155 may be moved to an unlocked position by retracting the lock member by a sufficient amount that it no longer protrudes into the space 134. With the resheathing lock member 155 in the unlocked position, the carriage assembly 140 may continue to move distally, thereby allowing for full deployment of the valve. Optionally, the locking member 155 may be designed to be fully removable from the frame 130 and disposable. Alternatively, the resheathing lock mechanism shown and described with reference to FIGS. 1 and 2, or any other resheathing lock mechanism having an appropriate configuration, may be incorporated into the operating handle 120 in place of the resheathing lock member 155.

The carriage assembly 140 has a longitudinal bore 192 extending partially therethrough and sized to freely and slidingly receive a threaded rod 194 therethrough. A pocket 193 extends vertically through the carriage assembly 140 for receiving a shaft adjustment nut 199 in threaded engagement with the threaded rod 194. The pocket 193 is sized and shaped to receive the shaft adjustment nut 199 with minimal clearance, such that the shaft adjustment nut remains substantially fixed relative to the frame 130 as it rotates on the threaded rod 194. Accordingly, rotation of the shaft adjustment nut 199 in one direction (either clockwise or counterclockwise depending on the orientation of the threads on the threaded rod 194) causes the threaded rod 194 to move proximally within the bore 192, and rotation of the shaft adjustment nut 199 in the opposite direction causes the threaded rod 194 to move distally within the bore 192. The threaded rod 194 has an interior bore extending longitudinally therethrough, the bore being sized to receive the proximal end of the inner shaft 126. The attachment of the inner shaft 126 to the threaded rod 194 includes similar structure as the attachment of the inner shaft 26 to the threaded rod 94 described above.

The operation of the operating handle 120 to deploy a prosthetic valve from the compartment 123 is similar to the operation of the operating handle 20 described above with reference to FIGS. 1-3. The user can rotate the deployment actuator 121 to slide the carriage assembly 140 distally within the elongated space 134 in the frame 130, which thereby pushes the distal sheath 124 distally relative to the compartment 123 and exposes and initiates deployment of the valve located therein.

After movement of the distal sheath 124 has partially revealed the compartment 123, the user may continue the deployment process without use of the deployment actuator 121 by squeezing the locking members 180 inwardly towards one another to release the coupler 160, and simultaneously pushing the coupler distally within the frame 130. As the coupler 160 is pushed distally within the frame 130, the linking of the coupler to the carriage assembly 140 through the threaded rod (not shown) and the deployment actuator 121 results in a concomitant distal movement of the carriage assembly, and with it, the distal sheath 124. Similar to the deployment process described above with reference to the operating handle 20, completing the deployment process while squeezing the locking members 180 may allow such process to be completed more quickly.

Since the resheathing lock member 155 is in the locked position, movement of the carriage assembly 140 distally may continue only until the distal end of the carriage assembly contacts the lock member. At this juncture, the distal sheath 124 will not be fully withdrawn from the compartment 123, and the prosthetic valve will not be fully deployed. Therefore, if the user desires to resheathe and reposition the valve before full deployment, the user can do so by rotating the deployment actuator 121 in the direction opposite that used for deployment until the carriage assembly 140 contacts the coupler 160.

If, during deployment, the user has partially deployed and then resheathed the valve, the outer shaft 122 and/or the inner shaft 126 may have become temporarily or permanently deformed, such that the respective distal ends thereof may be longitudinally displaced relative to one another. Such permanent deformation of these components may result in an inability of the distal sheath 124 to completely cover the compartment 123 such that the proximal end 129 of the distal sheath may not extend far enough to abut the retainer 127.

To adjust the relative longitudinal positions of the retainer 127 and the distal sheath 124, the user may rotate the shaft adjustment nut 199, causing the threaded rod 194 and the inner shaft 126 affixed thereto to slide proximally relative to the inner carriage 140. Because the distal sheath 124 is connected to the inner shaft 126 which, in turn, is connected to the inner carriage 140 and thus fixed relative to the frame 130, and because the retainer 127 is connected to the outer shaft 122 which is connected to the frame 130, sliding the inner shaft proximally relative to the frame will slide the distal sheath proximally relative to the retainer 127, which may continue until the proximal end 129 of the distal sheath contacts the retainer and the compartment 123 is completely covered.

Once the valve has been properly positioned, the deployment operation may be completed by withdrawing the resheathing lock member 155 to the unlocked position and moving the carriage assembly 140 further distally until the valve is fully deployed.

The operating handles described herein may be provided with a deployment locking mechanism. Such a deployment locking mechanism may prevent the accidental initiation of deployment by fixing the carriage assembly to the frame while the lock is in a locked position. Such a deployment lock may have a structure similar to the deployment locks shown and described in co-pending U.S. Patent Application No. 61/376,425, filed on Aug. 24, 2010.

Although the operating handles have been described herein as having one resheathing lock, any number of resheathing locks may be used, with or without a deployment lock, resulting in any number of stages in the deployment process. For example, there may be two, three, four, five, six or more resheathing locks, which thus enable the deployment procedure to be controlled incrementally. Such multiple resheathing locks may have a structure similar to the resheathing locks shown and described in co-pending U.S. Patent Application No. 61/376,425, filed on Aug. 24, 2010.

More particularly, if a user desires, for example, a two-stage deployment process, a single resheathing lock may be used, resulting in an unsheathing of perhaps about 80% to about 90% of the valve in a first deployment stage, followed by an unsheathing of the remaining about 10% to about 20% of the valve in a second deployment stage.

If the user desires a three-stage deployment process, on the other hand, a single resheathing lock may be used with a deployment lock, resulting in a first deployment stage in which no deployment can occur, a second deployment stage in which, for example, about 80% to about 90% of the valve is unsheathed, and a third deployment stage in which the remaining about 10% to about 20% of the valve is unsheathed.

Still further, if the user desires a four-stage deployment process, two resheathing locks may be used with a deployment lock, resulting in a first deployment stage in which no deployment can occur, a second deployment stage in which, for example, about 50% of the valve is unsheathed, a third deployment stage in which, for example, about 80% to about 90% of the valve is unsheathed, and a fourth deployment stage in which the remaining about 10% to about 20% of the valve is unsheathed. This last process may be modified to a three-stage deployment process by omitting the deployment lock while keeping the two resheathing locks.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of delivering a collapsible prosthetic heart valve in a patient, the method comprising:
    providing a delivery device having a catheter assembly and an operating handle, the catheter assembly including a compartment adapted to receive the valve in an assembled condition, the operating handle including a frame defining a movement space therein, a carriage assembly moveable in first and second opposite longitudinal directions within the movement space, a coupler, and a deployment actuator constrained relative to the coupler in the longitudinal directions, the coupler operatively coupling the carriage assembly to the frame, the coupler being selectively lockable to the frame in any of a plurality of fixed positions within the movement space;
    loading the valve into the compartment of the catheter assembly, the compartment and the valve being covered by a distal sheath of the catheter assembly;
    inserting the catheter assembly into the patient;
    positioning the valve at a target location within the patient;
    partially deploying the valve by rotating the deployment actuator to move the carriage assembly of the operating handle relative to the coupler and the frame in a first longitudinal direction along a first portion of the movement space, while the coupler is in a locked condition in which the coupler is connected to the frame in a fixed position; and
    fully deploying the valve by unlocking the coupler from the frame and translating the coupler together with the carriage assembly to continue movement of the carriage assembly in the first longitudinal direction along a second portion of the movement space.

2. The method of claim 1, wherein the operating handle further includes a resheathing lock having a locked position and an unlocked position, the resheathing lock in the locked position limiting movement of the carriage assembly in the first longitudinal direction to a stop location in the movement space, the resheathing lock in the unlocked position permitting movement of the carriage assembly beyond the stop location, the method further comprising adjusting a position of the resheathing lock in the first longitudinal direction to set the stop location in the movement space.

3. The method of claim 1, further comprising resheathing the valve by moving the carriage assembly in the second longitudinal direction.

4. The method of claim 3, wherein the catheter assembly further includes a first shaft around which the compartment is defined, the first shaft is operatively connected to the frame, the distal sheath is operatively connected to the carriage assembly, and the resheathing step includes moving the first shaft proximally relative to the frame and the distal sheath.

5. The method of claim 4, wherein the operating handle further includes a threaded rod operatively connected to the first shaft and extending in the first longitudinal direction, and a nut threadedly engaged with the threaded rod and longitudinally constrained relative to the frame, and the step of moving the first shaft includes rotating the nut about the threaded rod.

6. The method of claim 4, wherein the operating handle further includes a resheathing lock having a locked position and an unlocked position, the resheathing lock in the locked position limiting movement of the carriage assembly in the first longitudinal direction to a stop location in the movement space, the resheathing lock in the unlocked position permitting movement of the carriage assembly beyond the stop location, and the step of moving the first shaft is performed with the resheathing lock in the locked position.

7. The method of claim 3, wherein the catheter assembly further includes a first shaft around which the compartment is defined and an inner shaft connecting the carriage assembly to the distal sheath, the first shaft at least partially surrounding the inner shaft, the inner shaft and the distal sheath are operatively connected to the carriage assembly, and the resheathing step includes moving the inner shaft proximally relative to the carriage assembly.

8. The method of claim 7, wherein the operating handle further includes a threaded rod operatively connected to the inner shaft and extending in the first longitudinal direction, and a nut threadedly engaged with the threaded rod and longitudinally constrained relative to the carriage assembly, and the step of moving the inner shaft includes rotating the nut about the threaded rod.

9. The method of claim 7, wherein the operating handle further includes a resheathing lock having a locked position and an unlocked position, the resheathing lock in the locked position limiting movement of the carriage assembly in the first longitudinal direction to a stop location in the movement space, the resheathing lock in the unlocked position permitting movement of the carriage assembly beyond the stop location, and the step of moving the first shaft is performed with the resheathing lock in the locked position.

10. The method of claim 1, wherein the catheter assembly further includes a first shaft around which the compartment is defined and an outer shaft connecting the carriage assembly to the distal sheath and at least partially surrounding the first shaft, the first shaft is operatively connected to the frame, the distal sheath is operatively connected to the carriage assembly, and the steps of partially deploying the valve and fully deploying the valve each include moving the outer shaft proximally relative to the frame.

11. The method of claim 1, wherein the catheter assembly further includes a first shaft around which the compartment is defined, an inner shaft connecting the carriage assembly to the distal sheath, the first shaft at least partially surrounding the inner shaft, and an outer shaft connecting the frame to the first shaft and at least partially surrounding the inner shaft, the inner shaft and the distal sheath are operatively connected to the carriage assembly, and the steps of partially deploying the valve and fully deploying the valve each include moving the inner shaft distally relative to the frame.

12. The method of claim 1, wherein the target location within the patient is the native aortic annulus of the patient.

13. The method of claim 1, wherein the distal sheath of the delivery device is inserted through a femoral artery of the patient.

14. The method of claim 1, wherein the distal sheath of the delivery device is inserted through the apex of the heart of the patient.

15. The method of claim 1, wherein the step of partially deploying the valve includes rotating the deployment actuator to move the carriage assembly in the first longitudinal direction with a mechanical advantage, and the step of fully deploying the valve includes translating the coupler together with the carriage assembly in the first longitudinal direction without a mechanical advantage.

16. A method of delivering a collapsible prosthetic heart valve in a patient, the method comprising:

provbibling a delivery device having a catheter assembly and an operating handle, the catheter assembly including a compartment adapted to receive the valve in an assembled condition, the operating handle including a frame defining a movement space therein, a carriage assembly moveable in a longitudinal direction within the movement space, and a coupler operatively connected to the carriage assembly for movement therewith;

loading the valve into the compartment of the catheter assembly, the compartment and the valve being covered by a distal sheath of the catheter assembly;

inserting the catheter assembly into the patient;

positioning the valve at a target location within the patient;

partially deploying the valve by moving the carriage assembly of the operating handle in a first longitudinal direction along a first portion of the movement space, while the coupler is in a locked condition connected to the frame in a fixed position; and fully deploying the valve by unlocking the coupler from the frame and translating the coupler of the operating handle together with the carriage assembly to continue movement of the carriage assembly in the first longitudinal direction along a second portion of the movement space, wherein the operating handle further includes a threaded rod extending from the carriage assembly through the coupler, and a deployment actuator threadedly engaged with the threaded rod and longitudinally constrained relative to the coupler, and the partially deploying step includes rotating the deployment actuator.

\* \* \* \* \*